United States Patent [19]
Vanderveer et al.

[11] Patent Number: 4,777,045
[45] Date of Patent: Oct. 11, 1988

[54] HIGH BRAN SNACK

[75] Inventors: Fred Vanderveer, Mahwah; Robert Straka, Pequannock; Thomas P. Calandro, Paterson, all of N.J.

[73] Assignee: Nabisco Brands, Inc., Parsippany, N.J.

[21] Appl. No.: 759,317

[22] Filed: Jul. 26, 1985

[51] Int. Cl.$^4$ .................. A01N 65/00; A01K 35/78
[52] U.S. Cl. ........................... 424/195.1; 424/439; 426/72; 426/74; 426/94; 426/293; 426/559; 426/621; 426/808
[58] Field of Search ............ 424/439, 147, 156, 195.1; 426/2, 72, 74, 93, 94, 293, 559, 560, 618, 620, 621, 808; 514/251

[56] References Cited

U.S. PATENT DOCUMENTS

| | | |
|---|---|---|
| 1,173,932 | 2/1916 | Cockrell . |
| 1,210,589 | 1/1917 | Black . |
| 1,244,586 | 10/1917 | Cockrell . |
| 1,263,609 | 4/1918 | Schuyler . |
| 1,271,139 | 7/1918 | Dickenson . |
| 3,062,659 | 11/1962 | Vollink ................................ 99/80 |
| 4,327,116 | 4/1982 | Weith ................................. 426/19 |
| 4,350,714 | 9/1982 | Duvall ................................ 426/559 |

FOREIGN PATENT DOCUMENTS

| | | |
|---|---|---|
| 2837294 | 3/1979 | Fed. Rep. of Germany . |
| 1507867 | 4/1978 | United Kingdom . |
| 1561190 | 2/1980 | United Kingdom . |

OTHER PUBLICATIONS

Bruce, W. R. et al., "Strategies for Dietary Intervention Studies in Colon Cancer", Cancer, vol. 47, No. 5, (Mar. 1, 1981), pp. 1121 to 1125.

Cummings, J. H. et al., "The Effect of Meat Protein and Dietary Fiber on Colonic Function and Metabolism", Am. J. Clin. Nutr. 32:2086–2093, (1979).

Shah, P. J. R. et al., Idiopathic Hypercalciuria: Its Control with Unprocessed Bran", Br. J. Urology, 52:426–429, (1980).

Lineback et al., "Food Carbohydrates", (1982), pp. 296, 333 and 334.

Allen, L. H., "Calcium Bioavailability and Absorption: A Review", Am. J. Clin. Nutr., 35:783–808, (1982).

Primary Examiner—Michael R. Lusignan
Attorney, Agent, or Firm—Richard Kornutik

[57] ABSTRACT

A high bran snack, for the prevention of colon cancer, of which a typical formulation is: graham (whole wheat) flour, 40 percent; rice flour, 10 percent; whole wheat bran flour, 50 percent; calcium carbonate, 1.25 percent; reduced iron, 0.013 percent; and riboflavin (as a tracer), 0.02 percent. About 5 ounces of water is added per 80 ounces of dry materials. The dry materials are mixed in a ribbon blender and then fed dry into a cooker extruder. Then the water is added to the mixture in the extruder. The mixture is extrusion cooked and formed in, for example, a twin-screw cooker extruder. Each of the ingredients in the formulation has a processing, nutritional or therapeutic purpose. The extruded pieces are coated with coconut oil and powdered flavorant.

46 Claims, 1 Drawing Sheet

HIGH BRAN SNACK

BACKGROUND OF THE INVENTION

1. Field of the Invention

The invention relates to the consumption of dietary fibers to prevent the occurrence or recurrence of colon polyps and to prevent colon cancer.

2. Background Art

Observational epidemiological studies and clinical experiments have generated a number of hypothesis about the role of dietary factors in the etiology of colorectal cancer: fat and meat, especially beef, may enhance the risk, while fiber, cruciferous vegetables, lactose and vitamins C and E may protect.

According to Lineback et al., "Food Carbohydrates", (1982), page 296, there is not any completely satisfactory definition of the material which is generally referred to as fiber. The indigestible matter in animal feeds has always been designated as "crude fiber", and the term "dietary fiber" has been suggested for the plant cell wall constituents that are not digested by the secretion of the human digestive tract. The current definition of dietary fiber is not entirely satisfactory. There is a distinction between crude fiber and dietary fiber, since the former is a designation of a fraction determined analytically in a manner that gives an approximation of only cellulose and lignin and not of other cell-wall constituents not digested by man.

The substance that the lay public most readily equates with the term dietary fiber is wheat bran. Wheat bran is a heterogeneous substance which contains, in addition to fat and protein, at least 15 different minerals ranging from phosphorus and potassium at 1.04 and 1.38 percent, respectively, to iron (122 ppm), manganese (80 ppm), silicon (±ppm) and selenium (0.1 ppm). Burkitt, D. P., "Epidemiology of cancer of the colon and rectum", Cancer 28, 3, (1971); Burkitt, D. P., "Colonic-rectal cancer: fiber and other dietary factors", Am. J. Clin. Nutr. 31, S58, (1978), and Trowell, H., "Ischemic heart disease and dietary fiber", Am. J. Clin. Nutr. 25, 926, (1972), concluded from epidemiological observations that populations subsisting on high residue diets exhibted fewer of the diseases of Western civilization (cancer, heart disease and, gallstones). Cleave, T. L., "The neglect of natural principles in current medical practice", J. R. Nav. Med. Serv. 42, 55, (1956), suggested that modern day diseases were due to increasing intake of refined flour and sugar. It must be remembered that Burkitt and others were referring to a type of diet rather than a single component.

Epidemiologic studies have identified a low intake of dietary fiber as one of the factors associated with an increased rate of cancer of the colon [for example, see "Dietary fibre, transit time, faecal bacteria, steroid and colon cancer in two Scandanavian population", International Agency for Research on Cancer, Intestinal Microbiology Group, Lancet, July 30: 207-211, (1977), and Wynder, E. L., "The environment and cancer prevention", J. Environ. Path. Toxicol. 3: 171-192, (1980)]; other such studies include high intake of fat and animal protein [for example, see Armstrong, B., et al., "Environmental factors and cancer incidence and mortality in different countries with special reference to dietary practices", Int. J. Can., 15: 617-631, (1975)].

Different methods of estimating fiber consumption have lead to different conclusions about its association with national mortality: Lui, K., et al., "Dietary cholesterol, fat and fibre and colon-cancer mortality", Lancet, 782-785, (Oct. 13, 1979), found a negative association, while Draser, B. S., et al., "Environmental factors and cancer of the colon and breast" British Journal of Cancer, 27, 167, (1973), did not find such a negative association.

Retrospective studies designed to compare the dietary habits of colon cancer patients with controls have also failed to provide consistent evidence on the fiber hypothesis. Several of the studies have supported it [Bjelke, E., "Case control study of cancer of the stomach, colon and rectum", In Oncology (1970) Eds. R. L. Clarke, R. W. Cumley, J. E. McCay and M. M. Copeland. Proceedings of the 10th International Cancer Congress, Volume V, Chicago, Ill.: Year Book Medical Publishers Inc., (1971), p. 320; Modan, B., et al., "Low-fibre intake as an etiological factor in cancer of the colon", Journal of the National Cancer Institute, 55, 15, (1975); Graham, S., et al., "Diet in the epidemiology of cancer of the colon and rectum", Journal of the National Cancer Institute, 61, 709, (1978); and Dales, L. G., et al., "A case-control study of relationships of diet and other traits to colorectal cancer in American blacks", American Journal of Epidemiology 109 (2), 132-144, (1978)], while others have not [Higginson, J., "Etiological factors in gastrointestinal cancer in man", Journal of the National Cancer Institute, 37 (4), 527-545, (1966); Wynder, E. L., et al., "Environmental factors of cancer of the colon and rectum", Cancer 20, 1520-1561, (1967); and Jain, M., et al., "A case-control study of diet and colorectal cancer", International Journal of Cancer, 26, 757-768, (1980)].

Concerning the incidence of colon cancer seen in industrialized populations which has been associated with lack of dietary fiber, the presence of fiber in the intestinal tract decreases transit time, which reduces contact time between potential carcinogens and the mucosa, and it dilutes the intestinal contents and thus reduces the possibility of interaction of procarcinogens with bacteria. Although some epidemiological data would appear to bear out the above stated hypothesis, some investigators, working from the same data base, have found little correlation between dietary fiber but a strong correlation with ingestion of animal fat. However, a high fiber diet is usually a low-fat diet and vice versa.

Experimental studies have shown that some kinds of fiber can protect against chemically induced cancer. Rats fed stock diets had fewer 2-acetylaminofluorene-induced tumors than those fed semipurified diets. Colon cancer can be induced in rats by several compounds, including 1,2-dimethylhydrazine, methylnitrosourea and azoxymethane. Wheat bran has been found to protect rats against colon tumors induced by either injection [Fleiszer, D., et al., "Protective effect of dietary fibre against chemically induced bowel tumors in rats", Lancet 2, 552 (1978)] or oral administration of 1,2-dimethylhydrazine [Barbolt, T. A., et al., "The effect of bran on dimethylhydrazine-inducedcolon carcinogenesis in the rat", Proc. Soc. Exp. Biol. Med. 157, 656, (1978)]. In Watanabe, K., et al., "Effect of dietary alfalfa, pectin and wheat bran on azoxymethane or methylnitrosourea-induced colon carcinogenesis in F344 rats", J. Natl. Cancer Inst. 63, 141, (1970), rats were fed 15 percent alfalfa, pectin or wheat bran and the effects of an injected carcinogen (azoxymethane) in one group were compared with one administered by intrarectal instillation (methylnitrosourea) in another. Pectin and bran protected against azoxymethane-induced tumors but not against methylnitrosourea. Alfalfa did not affect the course of azoxymethane-induced tumors but significantly increased the incidence of methylnitrosourea-induced tumors. The data indicates that the action of dietary fiber was mediated by the mode of administration of the carcinogen.

The decreased intake of dietary fiber has been implicated as a factor in diseases such as cancer, diabetes and coronary disease. In the case of diabetes, increased dietary fiber definitely lowers plasma glucose and insulin levels. Data relating to heart disease and colon cancer are not as clear cut and must be assessed in the light of differences in total diet and lifestyle between populations at high and low risk. (Lineback et al., ibid., page 306.)

"FDA Studies Advertising For Kellogg's All-Bran—Linked to Cancer Prevention", The Washington Post, (Nov. 6, 1984), pages E1 and E4, states:

"The Food and Drug Administration has launched a preliminary review of a new advertising campaign by the Kellogg Co. that links its All-Bran cereal to cancer prevention."

"The Kellogg ad campaign is the first by a major food manufacturer to specifically link its product to cancer prevention, a claim the FDA fears may violate federal rules. Under FDA regulations, it is illegal to make health claims about specific foods without prior FDA approval."

"'Is this promotion, in its language, offering a drug because of the product's linkage to the disease called cancer?' said FDA spokesman Bruce Brown. If so, then Kellogg has failed to win FDA approval of All-Bran as a way to prevent cancer, Brown added." [p. E-1]

"However, Kellogg's All-Bran Advertisement represents the first time a major manufacturer has gone a step further and cited the quality of a specific food—in this case high fiber—as a way to prevent a specific disease."

"As a result, federal regulators say they are faced with a serious problem. On the one hand, Brown noted, they applaud Kellogg for bringing vital health information to the public. For the ad clearly points out that the 'National Cancer Institute believes a high fiber, low fat diet may reduce your risk of some kinds of cancer.'"

Nonetheless, Brown said, the claims may ultimately be considered misleading by federal regulators because it not include enough information. Although the promotion encourages consumers to eat All-Bran, it may give the impression that all consumers need to do to prevent cancer is to eat All-Bran."

"That it has apparently angered California's Cancer Advisory Council, which, under the auspices of the state's Department of Health Services, is currently drafting a letter to the FDA."

"State officials declined to talk about the letter, saying it was premature to discuss it since it had not been approved and mailed yet. Advertising Age, however, noted that *the cancer advisorycouncil was disturbed because there is no scientific proof that All-Bran prevents cancer.*"

"Kellogg officials, however, said that all they were trying to do was work with the National Cancer Institute to publicize the cancer awareness prevention project. 'We want to communicate the NCI report that says that a high fiber, low fat diet may reduce your risk of some kinds of cancer,' said Celeste Clark, director of corporate publicity. 'This is the first time Kellogg has mentioned cancer in its advertisements . . . We worked very closely with NCI in developing the advertising message.'" [Emphasis supplied][p. E-1 and p. E-5]

"Among the possible objections FDA could have, Brown said, was that there are many different types of cancer. Kellogg implies high-fiber is a good way to prevent all types of cancer."

"Additionally, Brown said, the claims don't say how to use All-Bran if it really is to prevent cancer." [p. E-5]

Physiological effects of dietary fiber ought to be neither simple nor uniform, because the human gastrointestinal tract can accommodate to altered conditions and shows large variability in its actions. It has been postulated that beneficial effects of fiber in the large intestine include a binding and dilution of injurious substances. Although food remnants in the human large intestine are thought to provide little if any direct nutrition, they serve as substrates for microflora.

Lineback et al., ibid., states:

"Following the reawakening interest in dietary fiber, the physiological as well as technological aspects of materials considered suitable supplements for fiber-enrichment in various food formulations have become the subject of many investigations. Attempts have been made to draw conclusions as to the relationships between the type of dietary fiber and its functional behavior under varying processing conditions. Because of the high individuality of the test material, drawing of generally valid conclusions proved to be a very difficult task. *It is now recognized that a thorough physical and chemical characterization of the fiber-rich material must preclude any valid prediction regarding its functional or physiological effects* (Parrott and Thrail 1978)."

"We are thus approaching the more advanced phase of research in this field, in which *attempts are being made to relate the functionally relevant physical and physicochemical properties of dietary fiber to its detailed chemical profile*, rather than to its total content or distribution of more or less arbitrarily defined fractions. *There is still a great deal of ambiguity surrounding these relationships.* Great complexitiy of the studied material, lack of uniform methodology, high risk of creating artifacts under in vitro conditions and disreprancies between in vitro and in vivo situations are mostly responsible for a hitherto unsatisfactory status of our knowledge on this subject." [Emphasis supplied] [pages 333 and 334]

There are some potential disadvantages to the use of dietary fiber. Fiber-rich diets appear to induce malabsorption of minerals. Another potential hazard of fiber is in respect to reduce energy intake and protein utilization. Other possible deleterious effects of fiber such as persorption or volvulus of the sigmoid colon do not seem to be an immediate problem in populations ingesting normal, well-balanced diets.

In the case of colorectal cancer, colorectal polyps might be a suitable precursor of malignant disease. There is evidence for the causal association of adenomatous polyps and adenocarcinoma of the colon. Briefly, the prevalence of adenomatous polyps in several countries follows the incidence of colon cancer.

Allen, L. M., "Calciium bioavailability and absorption: a review", Am. J. Clin. Nutr. 35: 783–808, (1982), discussed the question of the adverse effect of bran intake on calcium bioavailability. Particular reference was was made in Allen to Cummings, J. H., et al., Am. J. Clin. Nutr. 32: 2086, (1979), which described the creation of a negative calcium balance in a few controlled subjects on a high bran diet.

U.S. Pat. No. 1,173,932 (Cockrell) discloses a cereal breakfast food consisting of about 60 percent of wheat bran and the remainder corn meal and oats flour, the latter two items being added to make the bran more palatable. The bran is used for its laxative properties.

U.S. Pat. No. 1,210,589 (Black) discloses a bran biscuit or cake which contains shredded cereal and syrup for nutrition and to make the bran palatable. The shredded cereal can be corn, wheat or rice. About 37½ percent of bran is used in the formula. Black mentions that bran has laxative properties.

U.S. Pat. No. 1,244,586 (Cockrell) discloses a cereal breakfast food consisting of about 60 percent of wheat bran and the remainder corn meal, wheat and oats. The bran is used for its laxative properties.

U.S. Pat. No. 1,263,609 (Schuyler) discloses a self-rising pancake flour which contains ground rice bran, baking powder, wheat flour, soy flour, rice polish and salt. The mixture can include rice flour. The given example uses 22.5 percent of ground rice bran. The bran is used as a flavorant.

U.S. Pat. No. 1,271,139 (Dickerson) discloses a composition which includes bran (e.g., 15 percent), whole wheat flour, wheat flour, rye flour, etc. The composition is used to make biscuits.

U.S. Pat. No. 3,062,659 (Vollink) discloses an extrusion-cooked, ready-to-eat breakfast cereal flakes which can contain rice flour or bran. A moist comminuted starch-containing cereal mixture is passed through a cooker extruder, the expanded extrudate is tempered and then the cereal material is flaked and toasted. Example 2 uses a starting formula that includes 60 percent of ground whole wheat and 24 percent of bran.

U.S. Pat. No. 4,327,116 (Weith) discloses a bran bakery product from dough composed of 100 parts by weight of bran, 200 to 300 parts by weight of water and 2.5 to 15 parts by weight of carob bean flour (or other vegetable thickening agent). Other conventional dough ingredients such as flavoring agents can be used. Weith specifically mentions wheat bran and rye bran. The prior art section of Weith states that cereal fibers are used as casual therapy of obstipation and intestinal diseases.

U.S. Pat. No. 4,350,714 (Duvall) teaches a corn bran, extrusion-cooked, expanded cereal which further contains corn flour, oat flour, ground limestone, [i.e., $CaCO_3$], sugar, salt, soda, vitamin premix and colorant. Duvall states that wheat flour and rice flour can be present. Example 1 shows the use of 25 percent of corn bran flour, and the claims recite that sufficient ground corn bran is used to provide 3.5 to 10 weight percent of fiber. The extruded pieces are enrobed in a syrup which includes sugar, coconut oil and water.

British Pat. No. 1,561,190 (Weetabix) discloses a food mixture containing bran and a binding agent (starchy material or gum) is mixed with water. The mixture is extrusion cooked. The mixture (on a dry basis) contains 10 to 95 percent of bran. The mixture can also contain wheat and rice flours.

German O. S. No. 2,837,294 (Bories et al.) discloses an extrusion cooked foodstuff composed of bran, 20 to 80 percent of gluten, 5 to 20 percent, and the balance flour or starch, with the addition of 5 to 20 percent water after charging the mixture to an extruder.

Known foods containing bran include bran muffins and cereals, such as, All Bran, 100% Bran, Shreddies, Bran Flakes and Bran Crunchies. Wheat bran is found naturally in whole-wheat breads and cereals, can be bought separately for adding to other foods and is rich in dietary fiber.

BROAD DESCRIPTION OF THE INVENTION

An object of the invention is to provide a composition and process for the prevention of the occurrence and recurrence of colorectal polyps. Another object of the invention is to provide a composition and process for the prevention of colorectal cancer. Other objects and advantages of the invention are set out herein or are obvious herefrom the one skilled in the art.

The objects and advantages of the invention are achieved by the composition and processes of the invention.

The invention involves a food composition or snack in the form of extrusion-cooked extrudate pieces, for consumption by humans. The invention extruded, high bran snack includes:

(a) about 40 to about 70 weight percent of bran flour;
(b) about 20 to about 50 weight percent of whole wheat flour;
(c) about 5 to about 15 weight percent of rice flour;
(d) about 0.5 to about 3 weight percent of calcium carbonate;
(e) about 0.03 to about 0.005 weight percent of reduced iron; and
(f) about 0.1 to about 0.005 weight percent of riboflavin.

The weight percent of ingredients (a) to (f) are based on the total dry weight of the food composition. The invention of dietary wheat bran serves as a mens of prevention of the recurrence of colorectal polyps. This serves as a means for reducing the incidence of colorectal cancer.

The invention further includes the extruded, high bran composition or snack coated with a layer of an edible organic oil and flavorant in particulate form. Preferably the edible organic oil is coconut oil and the flavorant is in powder form. The layer of organic oil serves to adhere the flavorant particles to the extruded pieces. This form of the invention food snack is much more palatable and edible.

The invention high bran snack has been developed for the prevention of colon cancer and is being studied in a five-year test for effectiveness. The control (placebo) was to have only whole wheat flour, and the test composition was to have 50 percent of whole wheat bran and 50 percent of whole wheat flour. This was the first development. Riboflavin was added. The riboflavin was used as a tracer which can be detected in stool. Then commercially available flavorants were added to the extruded pieces. Then an edible organic oil, preferably, coconut oil, was sprayed onto the composition pieces to enhance the flavor and to provide adhesion between the flavorant and the snack. However, it was found that the test high bran formulation was too deficient in calcium and iron to be consumed on a regular basis in substantial amounts to effect prevention of colon cancer. So calcium carbonate was added along with reduced iron. The calcium carbonate and the reduced iron made the product very hard; this problem was solved by adding rice flour to the formulation. Corn meal might provide a softer texture also, but it may also alter taste. A leavening agent to provide a lighter texture would erratically expand the product. The product is produced in a Creusot Loire extruder, which is a twin screw extruder having heating means for cooking the formulation. A preferred final formulation has 40 weight percent of graham flour, 10 weight percent of rice flour, 50 weight percent of bran flour, 1.25 weight percent of calcium carbonate, 0.013 weight percent of reduced iron and 0.02 weight percent of riboflavin. All of the dry ingredients are mixed in a ribbon blender and are fed to the extruder dry. Additionally, about 5 ounces of water are added per 80 ounces of dry materials, which is approximately 4 to 5 weight percent. The water is added to the extruder after the blended dry ingredients. Preferably then the extrudate pieces then coated with the edible organic oil and the particulate flavorant is affixed to the extrudate pieces.

The biologidal plausibility of the association between adenomatous polyps and malignant disease is supported by the observation that the morphology of lesions varies from adenomas exhibiting microfoci of malignant tissue to obvious cancer with residual benign tumor at the edge. Also, the amount of benign tumor is inversely related to the amount of spread of the malignant disease. In addition, the size, histology and grade of the polyps are associated with the probability of occurrence of malignant tissue. Finally, cases have been documented in which an untreated adenomatous polyp has progressed to malignant disease. [Day D., et al., "The adenoma-carcinoma sequence, 58–71, in Pathogenesis of colrectal cancer", Morson, B., W. B. Saunders Co. Philadelpha, (1978)].

The primary advantage with colorectal polyps as the outcome measure of a randomized trial is that the study can be of a practical size. The prevalence of polyps in Western man is high, approaching 50 percent at 70 years of age. A small trial studying the recurrence of polyps can be as sensitive as a large trial in which the outcome is death from colon cancer. The study of the recurrence of polyps offers an additional practical advantage; when patients with colorectal polyps are routinely examined every two or three years with fibreoptic colonoscopy, studies can be carried out between two colonoscopic examinations with essentially no additional medical cost or morbidity. The investigation given in detail below is therefore designed as a randomized trial to examine the role of a dietary fiber supplement in the recurrence of colorectal polyps, among patients who have had at least one adenomatous polyp removed by polypectomy.

An important advantage of the composition of the invention is that its continued consumption by humans prevents the recurrence of colon polyps, which are a problem themselves and which confer a high risk of colon cancer. A low fiber diet has been identified as one of the factors associated with an increased risk of cancer of the colon. The consumption of bran fiber prevents the recurrence of polyps in people with this problem. Polyps are not cancers, but sometimes they do become malignant.

The use of dietary fiber in the invention composition is important because it is one of the dietary components which can be manipulated to confer protection against colorectal cancer without making the diet unacceptable.

DETAILED DESCRIPTION OF THE INVENTION

Figure 1:
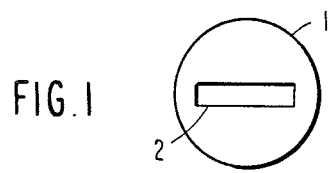
FIG. 1 is a front schematic view of an extrusion die used in the preparation process of the invention.

As used herein, all parts, percentages, ratios and proportions are on a weight basis unless otherwise stated herein or otherwise obvious herefrom to one skilled in the art.

Dietary fiber is widely distributed in unrefined cereals, fruits and vegetables. However, previous studies [Armstrong et al., ibid., and Maruchi, N., et al., "Relation of food consumption to cancer mortality in Japan with special reference to international figures", Gann 68: 1–13, (1977)], as well as our own recent review of international data, show that cereals rathe than fruits and vegetables correlate best with color cancer death rates. Our review of international data also found that, according to such data, total cereal seems important rather than any single type of cereal.

There are two general classes of products provided by a wheat mill, namely, flour and millfeed. These two general classes are subdivided into products depending upon the degree of purity desired. The subclasses for straight flour are patent flour (less than 70 percent of wheat) and clear flour (residue left when a patent flour is removed from a straight flour). The subclasses for millfeed are bran (seed coat material left after milling flour), germ (wheat seed embryo) and shorts (everything left after the bran and germ have been removed from millfeed).

The absolute amount of fiber in the invention used is well within the range found in diets in many parts of the world. The amounts have been used previously with no reported ill effects. [Cummings, J. H., et al., "Changes in fecal composition and colonic function due to cereal fibre", Am. J. Clin. Nutr. 29: 1468–1473, (1976)].

The following is the protocol used in a short preliminary study of invention products designed for use in a subsequent long term study:

Test Products

Two test products were developed. The lower fiber one was made from wheat flour and contained about 6.5 grams of dietary fiber per 100 grams. The other test product contained equal amounts of wheat flour and wheat bran for a total of 26.5 grams of dietary fiber per 100 grams of the product. The bran used corresponded to the composition of the AACC Standard Bran currently used as a reference. The test products were intentionally low in calories (about 150 Kcal and 200 Kcal per day for the lower fiber and higher fiber products, respectively) in order to make little contribution to the total intake. The products were also developed as snacks to avoid systematic replacement of any one food or group of foods. The snacks were covered with a light coat of oil and one of four flavors selected by a preliminary taste panel. They were also coated with riboflavin or riboflavin phosphate (equivalent of 30 mg riboflavin per package, e.g., 100 grams of the higher fiber product and 50 grams of the lower fiber product). The excretion of riboflavin by the human test subjects served as a marker of intake.

Human Test Subjects

The human test subjects were adults recruited from the volunteers at certain hospitals. They were between 45 and 70 years of age, which is a range that corresponds to that expected in the study of polyp patients. These subjects did not have any gastrointestinal problems which might affect their tolerance to fiber, were not taking any antibiotics or laxatives and were not on any therapeutic or self prescribed diets. The subjects were approached through volunteer coordinators, the study was explained to them and those wishing to participate were asked to sign a consent form.

Test Procedures

At the beginning of the study, a short diet and health history was obtained which served to:
1. identify those who should be excluded from the study because specific diseases, gastrointestinal surgery, use of laxatives or therapeutic diets;
2. characterize the study group;
3. sensitive them to their seating habits and methods of recording food intake as required in the study.

Forty volunteers were assigned to one of Group A or Group B (20 each). The volunteers consumed the two products according to the following schedule:

TABLE I

| Weeks | Group A | Group B |
| --- | --- | --- |
| 1 | 25 g of low fiber | 50 g of high fiber |
| 2 to 6 | 50 g of low fiber | 100 g of high fiber |
| 7 | 50 g of high fiber | 25 g of low fiber |
| 8 to 12 | 100 g of high fiber | 50 g of low fiber |

The human test subjects were instructed in keeping four day food records (two week days and a weekend) and they kept these records before they started the products and at 3, 6 and 12 weeks. The records were checked to determine whether there has been any apparent change in eating pattern due to the consumption of the snacks.

The subjects were also asked to keep a daily health/food record throughout the study. This record included an estimate of the amount of product eaten each day. The subjects were asked to return any uneaten bags of snacks or portions of bags as a further estimate of actual consumption.

At the end of the study of short questionnaire was complete. The questionnaire contained questions on the use of the products, which if any foods were replaced by them, and a subjective evaluation of ability to continue to consume the products.

The subjects also supplied samples as follows:

TABLE II

| Time, Weeks | Sample | Analysis | Purpose |
| --- | --- | --- | --- |
| 0 and 12 | venous blood | hemoglobin ferritin | check for any possible effect on iron status |
| 0, 3, 6 and 12 | 14 hour urine | riboflavin phenols | marker for intake indicator of transit time |
| 0, 3, 6 and 12 | breath | hydrogen and methane | indication of GI bacterial activity |
| 0, 6 and 12 | feces | pentane and other breath gases mutagen by the Ames Assay bile acid, cholesteral and degradation products | indication of lipid peroxidation in body potential carcinogen potential cancer promoters |

Sample Collection And Analysis

On the designated days, the volunteers were asked to void at 6 p.m. and discard the sample. All subsequent voiding, until 8 a.m. were pooled and collected in coded brown glass bottles. These bottles were brought to the hospital and placed in a freezer provided. They were collected and analyzed by HPLC for urinary phenols and riboflavin.

On designated days, each volunteer was asked to breathe purified air for two minutes through a mouth piece prior to supplying a breath sample by flowing into a tube provided for such. Samples were collected in large syringes and analyzed directly for hydrogen, pentane, methane and other gases by means of gas liquid chromatography.

Samples of feces were collected in coded plastic containers stored in dry ice boxes and stored in the freezers. The samples were transferred to a deep freezer ($-70°$ C.). At an appropriate time thereafter, the samples were extracted and tested for mutagenicity (Salmonella typhinurium TA-100) and for the presence of the mutagen by HPLC and U.V. spectra. Aliquotes were sometimes analyzed for bile acids, cholesterol and cholesterol derivatives (cholestanol and cholestanone).

Analyses

The first objective of the test was to ascertain the acceptability of the products, judged by as follows:

the number of subject consuming 50 percent or more of the product each day of the study;

the changes in the diet introduced by use of the product as measured by the food intake records; and the subjective evaluation of the subjects of their ability to continue using the products.

The second objective of the test was to collect preliminary biochemical data to be used as a basis for determining what, if any, analyses should be made in the intervention trial (long-term test described below).

Miscellaneous Matters

In some prior art short term studies, bran had decreased the absorption of calcium, iron, copper, zinc and magnesium, although the results were not always consistent. Because anemia is sometimes a problem among the test age group, the iron status of the subjects was monitored, with hemoglobin checks and with analysis of ferritan status at the beginning and end of the study. The methods available for assessment of other trace minerals was not considered accurate at the moment. They were also not necessary for such a short term study because the negative mineral balances are small in comparison with body stores and, therefore, of no clinical significance for the short time period.

The following is the protocol used in a long term study of the invention products. The investigation involved a clinical trial of dietary bran in the prevention of the recurrence of colorectal polyps. The investigation was designed as a randomized trial to examine the role of a dietary fiber supplement (i.e., invention product) in the recurrence of colorectal polyps, among patients who had previously had at least one adenomatous polyp removed by polypectomy.

Objectives Of The Test

The first objective of the test was to determine the feasibility for clinical use of increasing daily fiber intake by means of a dietary supplement.

The second objective of the test was to determine the effect of a dietary supplement of fiber (a) on the recurrence of gastrointestinal polyps and (b) on a number of biochemical parameters.

Summary Of Design

The investigation was and is being conducted as a randomized controlled trial. The human subjects are about two hundred consecutive patients who have had one or more adenomatous polyps identified and removed by colonoscopy at certain hospitals.

After the polypectomy, each eligible patient was informed of the study of his/her surgeon, was given a pamphlet summarizing the proposed investigation and invited to participate. Patients who wished to participate were interviewed at home—a detailed nutritional interview was conducted and samples of urine and blood were collected. The patient was provided with a supply of either (i) a supplement of wheat fiber (equivalent to over 26.5 grams per day) or (ii) a low fiber placebo supplement (equivalent to less then 4.0 grams per day). See below for the development of the full ingredient lists of the two compositions used in the test. Random allocation to the high or low fiber groups was made. The interviewer was initially blind to the allocation of the patients.

Each patient was contacted at regular intervals by the interviewer who collected information on diet and health and obtained urine and blood samples according to a pre-arranged schedule.

Two years after the initial colonoscopic examination, the patient was re-examined by the surgeon who performed the initial examination. Finds from both examinations were compared to ascertain any change in the number of polyps. The extent of this change was compared for the treatment and placebo groups. This long term study is still being conducted.

Details Of Investigation—Eligible Subjects

A patient was considered eligible for the study if the patient had at least one adenomatous (based on the final pathological report) polyp identified in the colon or rectum at the time of the intial colonoscopic examination, and (a) was under 75 years of age and resident in a certain area;
(b) had no history of previous bowel disease (except polyps), previous bowel resection, or familial polyposis, was not currently anemic and was not a regular user of laxatives;
(c) had no evidence of malignancy requiring bowel resection; and
(d) was not currently on a medically supervised diet for renal, liver or gallbladder disease. Any patient who satisfied the above criteria was not included if, in the documented opionion of the colonoscopist, inclusion in the study would be detrimental to the patient's health.

The study involved about 216 patients equally allocated at random into each of the high and low fiber supplement groups. This is based on an estimated rate of recurrence of gastrointestinal polyps of 24 percent in the low fiber group and a recurrence rate of 8 percent in the high fiber group. It was anticipated that approximately one hundred eligible patients are seen each year at the involved hospitabls. If 80 percent of eligible patients were willing to participate in the study, the required number of patients would be enrolled over a two to three year period.

Initial Medical Examination

Prior to each colonoscopy clinic, patients was be identified with appointments.

During each colonoscopic exmaination, the physician completed the colonoscopy form. For patients with a polyp, a polypectomy was performed and a quick pathological section examined immediately. A complete pathological examination of all polyps was subsequently conducted by a single pathologist. For each patient with a polyp considered to be adenomatous by the quick pathological section, the physician established whether the patient was otherwise eligible for the trial. After a suitable period of recovery from the colonscopy, the physician informed each eligible patient of the possibility of participating in a study. The patient was given a pamphlet describing the study and proposing that the patient be called to discuss the patient's participation. To confirm that a patient was eligible for the study, the complete pathology report for each patient was obtained and read; when there was mention of malignancy, the colonoscopist was consulted as to whether a bowel resection was indicated.

After ensuring that a patient was eligible for the study, and if the patient agreed to be interviewed, the patient's identifying information (including age, sex and colonoscopist) was passed to a designated study coordinator. If the patient refused to participate, the reason for refusal was recorded and the coordinator informed.

Study Coordination

For all patients, the study coordinator verified the eligibility or ineligibility of all patients by reviewing all colonoscopy forms and kept records of the proportion of eligible subjects who do not agree to a first meeting with the interviewer.

For eligible patients who agree to participate, a designated interviewer was given the patient's name, address and telephone number. The randomization process, described below, was conducted and the interviewer was provided with the fiber supplement appropriate for each patient. After each interview, the completeness and accuracy of all documents was checked and it was ensured that specimens were sent to the appropriate laboratory. When the laboratory results were obtained, all follow-up visits were coordinated.

Randomization

Patients were stratified by surgeon, sex and age. Within each stratum, patients were randomly allocated to receive the high or low fiber supplement using appropriate statistical methods of random allocation.

Fiber Supplements

Two test products were developed: namely, a low fiber snack composed primarily of whole-wheat flour and a high fiber snack made of equal parts of whole-wheat flour and wheat bran. The low fiber snack is a control. The snacks were to be sprayed with five percent oil alone or with the oil plus one of four flavors selected by an informal taste panel. Initially the snacks were also to be coated with riboflavin phosphate (30 mg per 50 grams of low fiber snack and per 100 grams of high fiber snack). The excretion of riboflavin in the urine serves as one test of compliance to the regimen. The contents of the extrudates and the coatings on the extrudates changed before the long term test started and during the long term test—the history thereof and the ingredient changes are chronologed below. The low fiber product was to be used in amounts of 50 grams per day (3.3 grams of fiber) and the high fiber one as 100 grams per day (26.5 grams of fiber).

Interviews

Interview were conducted in the patient's homes according to the following schedule:

TABLE III

| INFORMATION | CONTACTS (MONTHS) | | | | |
|---|---|---|---|---|---|
| | 0–.25 | 2 | 12 | 18 | 24 |
| Consent Form | x | — | — | — | — |
| Food Frequency Questionnaire | x | x | x | — | x |
| Health Status Record | x | x | x | x | x |
| Pin-Prick Hb. Test | x | — | x | — | x |
| Blood For Iron-Status Workup | x | — | — | — | x |
| Urine Riboflavin | x | x | x | x | x |

At the first visit, the study was described to the prospective participants and provided samples with of the snacks to taste. The patient was then asked whether the patient wished to continue in the study and, if so, the consent form was signed. The participants provided samples of urine and blood for initial biochemical analysis. The participants were provided with a week's supply of the appropriate fiber supplement and an appointment was made to return the next week to deliver the first batch of snacks, to administer a food frequency questionnaire and to complete a health status record.

Further interviews will be conducted by the same data collector and information and samples were collected for biochemical measurement. At each meeting, the unused snacks were collected—their quantity was a measure of the level of compliance to the dietary regime. Depending on the results of an initial evaluation of the fiber supplement, a sample of participants was also asked to provide samples of breath gases and feces for biochemical analysis.

Final Medical Examination

Two years after the initial medical examination the patient was re-examined by colonoscopy by the same surgeon. The logistics of such examination were similar to the initial examination. The surgeon completed a colonoscopy form, which was sent to the study coordinator, together with the pathology report. When symptoms lead to early recognition that polyps may have recurred, the patient received the second colonoscopy at whatever time was chosen by the surgeon to be appropriate for the patient's medical care.

Withdrawal of Subjects

Withdrawal of the patents from the study could occur in a number of circumstances:

(1) the patient wished to discontinue his participation and did not continue to receive the dietary supplement. Patients were informed that they could withdraw from the study at any time;

(2) the patient developed a condition which made continuation on the fiber supplement inappropriate or developed signs or symptoms of a side effect of the fiber supplement. (Serious side effects of the fiber supplements were not anticipated. The amounts of fiber in the high fiber have been used in several studies without serious ill effects. This level of consumption will likely increase the number and volume of stools produced and may also result in mild gas pains and increased flatulence until the individual adapts to the high fiber intake. Some studies have suggested that intake at the levels of the high fiber supplement has decreased adsorption of calcium, iron, copper, zinc and magnesium but other studies have not confirmed this effect. Because methods of assessment of most trace minerals are not reliable, only iron status was monitored in the present investigation.) If the patient develops any condition which might necessitate the withdrawal of the patient from the investigation, the testers were notified. The health of the participants was also monitored through assessment of hemoglobin and iron status.

(3) the patient developed symptoms which lead to the identification of recurrent polyps before the examination scheduled two years after the start of the study. These patients received normal medical care for the diagnosis and treatment of the recurrent polyps. After such a diagnosis, patients did not continue in the trial and did not receive the dietary supplement; or (4) the patient did, moved or for some reason failed to attend the final colonoscopic examination. Such patients received the fiber supplements for the entire period during which they were in contact with the testors.

Monitoring the Results of the Trial

The health of individual subject were monitored at intervals during the study and subjects were withdrawn if they develop side effects of the fiber supplements. The rate of occurrence of any serious side effects in the high and low fiber groups was compared (consideration was to be given to terminating the trial if the rate appeared appreciably higher in eithr group).

In addition, consideration was given to the possibility of monitoring the results of the trial as it is running to determine whether, contrary to expectation, polyps recur more frequently among subjects receiving the high fiber diet. The findings from such an intermediate data analysis would, however, be difficult to interpret because it is conceivable that the high fiber diet may lead to the early detection of polyps which have recurred by causing them to bleed (indeed, high fiber diets are used prior to the hemocult blood tests to precipitate bleeding). If a detection bias of this nature were to occur, it might be falsely concluded from an early analysis of the data that the high fiber diet was causing a higher rate of recurrence of polyps than the low fibers supplement. For this reason, it was proposed that the data will be analyzed only after completion of the study for all 216 patients who will be enrolled.

ANALYSIS

First Objective

The feasibility of increasing dietary fiber intake by means of a daily supplement was assessed in terms of:
(a) the proportion of eligible patients who refused to enter the trial;
(b) the proportion of patients on each regime who requested to be withdrawn from the study prior to completion but who have no medical reasons for so doing;
(c) the levels of compliance estimated from the average levels of riboflavin in the urine and from the quantity of unused snacks returned by the patients.

The use of the fiber supplements will be considered to be feasible for potential clinical use if at least 75 percent of the patients are willing to enter the trial and if at least 75 percent of those assigned to the high fiber regime consume an average of at least 50 percent of the supplement each day for the two year period.

Second Objective

The effect of the dietary supplement was assessed as follows: patients will be classified as having polyps which recurred or did not recur; recurrence rates will be compared by Cox regression analysis for the treated and placebo groups, taking account of confounding variables and premature withdrawal of study subjects.

If the fiber supplement is found to reduce the rate of recurrence of polyps, it will be concluded that fiber consumption plays a role in the etiology of gastrointestinal polyps and in consequence may play a role in the etiology of colorectal cancer.

If the fiber supplement is not found to reduce the rate of recurrence of polyps, it is possible that either (i) fiber consumption of the amount given here is not related to the etiology of polyps or (ii) the initiation of the polyps occurred before the intervention with the fiber supplement so that the lag time necessary for expression of the polyps was greater than two years; this would imply that the fiber intervention after the polyps had been identified was too late to affect the process.

Confounding Variables

Data from the food frequency questionnaire was combined to provide measures of ten dietary components: fat, fiber, lactose, cruciferous vegetables, pulses, vitamin C, caffeine, alcohol, red meat and other meat. These ten variables were recorded at the start and end of the study, and at two intermediate points; each variable was averaged over the study period, with weights reflecting the duration of the eating habits. For each variable, the starting value and the average value during the study were used as confounding variables in the analysis. Age, sex and surgeon were also confounding variables. Compliance was assessed from urine samples and from counts of supplement packages consumed at 2, 12, 18 and 24 months. An index of compliance was obtained at each point in time and these were averaged over the study period. This average compliance index was an additional confounding variable.

Withdrawal

Patients who withdraw from the study were treated in the analysis according to the reason for withdrawal:

(a) Those who withdraw from the dietary regime before completion of the study but who undergo the final endoscopic examination two years after the initial examination were analyzed as if they had completed the study: their compliance index reflected the length of time on the dietary regime.
(b) those who developed symptoms which lead to the identification of recurrent polyps, and hence to withdraw from the study before two years, were counted as 'failures' in the Cox analysis at the time of recurrence.
(c) For those who failed to undergo the final colonoscopic examination but either continued on the dietary regime from a two year period or withdrew early, it was not known whether they developed recurrent polyps during the study period. They were, therefore, analyzed first under the assumption that polyps did recur and then under the assumption that polyps did not recur. In both analysis, the compliance index indicated the duration of use of the dietary regime. It is hoped that there will be so few of these patients that analysis under both assumptions will not substantially alter the conclusions.

Third Objective

A subsidiary objective of the investigation was to examine the effect of the different dietary supplements on biochemical measurements, in order to ellucidate the mechanism of action of fiber. The precise biochemical measures could not, however, be determined without the results of the above-described prelinary evaluation. Based on the results of such preliminary study, samples of blood, feces, urine and breath gases were collected and analyzed to determine change in levels of the defined biochemical parameters from start to completion of the investigation. The changes were compared for the subjects on the high and low fiber supplements, taking into account the confounding variables.

The long term test has been going on for several years and is not yet completed.

Initially an extruded snack food of about one to two mm. thick and one to two cm. square was to be produced using a Creusot Loire BC 45 extruder. These products were to be made on a Creusot Loire extruder, model. A barrel temperature of 180° C. and die face pressure of 500 to 1500 psi was to be used, and sufficient water was to be added to yield an air dried product of 7 to 10 percent moisture. The screw profile was to be typical for starch extrusion. The extrudate (mainly flour) was to be forced through slot dies and then to be cut at the die surface. The hot product was to be tumbled with powdered flavorant and air dried. The samples could be packed in 50 to 100 g poly sleeves, 24 to a cardboard box. The formulations were to be:

(1) Bran Product:
  Bran: 50 weight percent
  Whole Wheat: 50 weight percent
(2) Control Product:
  Whole Wheat: 100 weight percent With both formulae, there was to be 30 mg of added riboflavin per 100 g of raw material. It was found that the riboflavin colored the product bright yellow. Riboflavin was to be analyzed in the subjects to insure that the high fiber snack was consumed. It was found that the placebo containing only wheat flour and was brown in color. The flavorant coatings were to be added and tumbled onto the hot extrudate at levels of 3 to 6 weight percent for the bran product and control, respectively. Both snacks were found to have a high bulk density.

The flavorants, produced by Givaudan Limited, Toronto, Canada, were to be: SPL4047 B.B.Q. (barbeque) powder, salt content 36–40 percent; SPL4048 beef & onion powder, salt content 38–42 percent; SPL4032 natcho powder, salt content 23–37 percent; and SLP4049 taco powder, salt content 42–46 percent. Both products were to be coated with seasonings obtained from space/flavor companies to make a four or five variety line. The snacks were to be small (about 1 cm squares) to discourage using them with dips. A metalized foil pouch was to be used since the product shelf life had not been tested. One year was desired and a good package material would be a safe way to insure such stability.

Analysis of the whole wheat and bran was:

TABLE IV

| Items | Whole Wheat, Percent | Bran, Percent |
|---|---|---|
| Dry Matter | 90.03 | 93.69 |
| In the dry matter: | | |
| Total Ash | 3.34 | 5.52 |
| Crude Protein | 17.78 | 17.50 |
| ADF-CP | 0.63 | 0.48 |
| Cell Wall | 6.53 | 26.28 |
| Hemicellulose | 4.38 | 16.81 |
| Cellulose(s) | 1.47 | 6.47 |
| Cellulose (ks) | 1.49 | 6.26 |
| Lignin (k) | 0.60 | 2.92 |
| Lignin (s) | 0.65 | 2.53 |
| Lignin (sk) | 0.38 | 1.43 |
| Cutin (ks) | 0.13 | 0.25 |
| Cutin (sk) | 0.27 | 1.10 |

Notes:
(a) Dry Matter - sample dried at 100° C.
(b) Total Ash - sample ashed at 550° C.
(c) Crude Protein - total skeldahl nitrogen × 6.25
(d) ADF-CP - nitrogen in the acid detergent fiber × 6.25 (bound, Maillard, unavailable)
(e) Cell Wall and Constiuents - done sequentially [Robertson and Van Soest, (1980)]
(f) Sequence 1:
(g) Sample ND → AD → 72% $H_2SO_4$ → $KMnO_4$ → Ash
(h) Sequence 2:
(i) Sample ND → AD → $KMnO_4$ → 72% $H_2SO_4$ → Ash
(j) Does not seem to be any damage from processing.

As noted above, the feeding study was to involve 200 people who have previously undergone surgery to remove colon polyps. The test population was to be divided into 100 people receiving snacks fortified with wheat bran and 100 people receiving a placebo without bran. Each person would be on the diet for two years. Three years worth of polyp patients from the involved hospitals would be required to get a sample size of 200 people and, allowing two years per patient, the total study would take five years.

The whole-wheat-and-bran snack, which was to be extruded from 50 weight percent of wheat bran, with approximately 50 percent of whole wheat flour, including 0.2 weight percent of riboflavin (20 mg per 100 gm of finished product), had the desired size, density and shape for the subsequent operation of adding oil, flavor and eventually packaging. Samples of finished products, with 4 different flavors, applied at a level of 3 weight percent to the extruded base product, with the addition of 3 weight percent of vegetable oil, as well as samples without oil, were examined by several people. The consensus decision was that the oil addition significantly improved adhesion of the flavor particles, enhanced flavor acceptability and improved mouth feel organoleptically.

The whole wheat snack, which was extruded from whole wheat, including 0.4 weight percent of riboflavin (20 mg per 50 gms of finished product) was puffed slightly so that a 50 gm volume of the product had approximately the same volume as 100 gm of the 50 percent bran product. Snacks with and without 5 to 6 weight percent of vegetable oil and 4 flavors were examined by several people. The consensus decision was preferance of the oil addition. The flavor used at 6 weight percent in the product, so both the oil and flavor in 50 gms of the snack represented the same intake as 100 gm of the whole-wheat-and-bran snack.

The riboflavin in both series of such snacks was added via a water addition into the feed of the extruder. This apparently resulted in uneven riboflavin distribution, visible as yellow "spots" on the products. The distribution was greatly improved by blending the riboflavin with the other powder components prior to feeding to the extruder, thereby eliminating the problem.

The oil is a definite advantage to the products and preferably the most stable vegetable oil possible is used. Coconut oil (with a low iodine number) is preferred. The sprayed snacks have shelf life of at least 6 months against rancidity. The level of 3 percent on the 50 percent bran product, and 6 percent on the whole wheat product, represent an intake of 3 gms of oil per day for the people taking either snack product, equivalent to 27 kilo calories per day or about 1 percent of total daily caloric intake. The 5th "flavor" was an unflavored snack which also had oil, but with no flavor added. Packaging with plastic bag, laminated foil-plastic film bags and metalized mylar film bags were satisfactory. Uniformity of the package weights was important for the long term test program.

The inclusion of the food grade vegetable oil significantly improves adhesion of the flavor particles, enhances flavor acceptability and improves mouth feel organoleptically. The procedure involves heating the mass of extruded snack product coating such material with heated oil uniformly (e.g., by spraying) and adding the finely powdered flavors. About 1 to about 10 weight percent, preferably about 3 weight percent, of vegetable oil is used and about 1 to about 10 weight percent, preferably about 3 weight percent, of flavorant is used—in each case the weight percent is based on the weight of the extrudate.

The prior procedure for applying the seasoning (flavorant) to hot moist product directly out of the extruder, bulk packed and shipped to a copacker was found to be unsatisfactory. It was found that most of the seasoning vibrated off the product during shipping and packaging operation. Accordingly, the unseasoned product is heated, a light spray oil applied and then seasoned.

Analysis of the snack products was:

TABLE V

| Items | Low Fiber Snack, percent | High Fiber Bran Snack, percent |
|---|---|---|
| Moisture | 6.06 | 6.36 |
| Ash | 1.66 | 4.21 |
| Protein (N × 5.7) | 16.02 | 19.40 |
| Fat | 1.48 | 2.61 |
| Fiber | 1.19 | 6.02 |

Analysis of the Givaudan seasoning for Lipase Activity produced the following results:

TABLE VI

| | |
|---|---|
| Barbeque Powder (SPL 4047) | 0.010 percent |
| Beef & Onion Powder (SPL 4048) | 0.006 percent |
| Nacho Powder (SPL 4032) | 0.025 percent |
| Taco Powder (SPL 4049) | 0.011 percent |

The results were typical for seasonings.

The subjects on the preliminary trial seemed to be at the lower normal range of calcium to start, so as not to "stress" their calcium intake it was decided to add calcium to the snack from whole wheat and wheat bran. Some similar thoughts related to iron intake also. So the whole-wheat-and-bran snack product was further developed by adding calcium and iron. 10 mg of iron, in the form of reduced iron was added per 100 gm of finished product package. The level was intended to supply an entire RDA of iron, to compensate for any adverse effect of bran on bioavailability. (Types of food grade iron are the electrolytic iron, Electrolytic Iron A-131, and the reduced iron, Reduced Iron 716, of Glidden-Durkee. Both of such irons are amorphous, elemental iron powders.) Two levels of calcium were to be tried by adding different amounts of calcium carbonate (40 percent calcium content). The first level is 200 mg calcium per 100 gm product, from 550 mg. calcium carbonate, or 0.5 percent calcium carbonate in the product. The second level is 500 mg calcium per 100 gm product, from 1250 mg calcium carbonate, or 1.25 percent calcium carbonate in the product. It is also decided to add 100 mg of calcium, from 250 mg of calcium carbonate to each package (50 gm) of daily intake of the low fiber control product. This is about 0.5 percent of calcium carbonate in the control product. Calcium monophosphate could also be used.

A suitable wheat bran typically contains 40 weight percent of dietary fiber, 15 weight percent of protein, 4 weight percent of fat and 3 weight percent of ash, and a moisture content of 12 weight percent. Examples of suitable brans are wheat bran (which is preferred), rye bran, oat bran, corn bran and durum bran.

It is decided not to use soy sauce as an ingredient in the high bran composition. Samples of the 50 percent bran snack made with soy sauce used at 7 ounces of soy sauce per 8 pounds of dry product, equivalent to 5.5 percent soy sauce are organoleptically excellent. Tests marked improvement in manufacturing characteristics with the soy sauce. Most of the ingredients soy sauce pose no problem, but the salt content however does. The sodium content of soy sauce is 7.325 percent, equivalent to 18.8 percent of sodium chloride. Considering that soy sauce has only 63 percent water content, this represents essentially a saturated solution (30 percent salt) in the available water. Used at 7 ounces of soy sauce per 8 pounds of finished dry product (5.5 percent), this 18.8 percent salt content calculates to slightly over 1 percent salt content (1.03 gm of salt per 100 gm of finished dry product) the finished bran snack. This poses problems for an "unflavored" snack, which is surprisingly then the flavorant.

Next is the solving of the texture and taste problems of adding calcium carbonate at 1.25 percent to the product, equivalent to about 0.5 percent of calcium content, to contain 500 mg of calcium per 100 gm of daily intake of the high bran product. The addition of reduced iron at 10 mg per 100 gm of the finished high bran product (0.01 percent) seems to present no problems. For the low fiber control, the addition of 0.5 percent of calcium carbonate, equivalent to about 100 mg calcium per 50 gm of low fiber product in the finished package, would seem to offer no problem, as the problems have apparently been solved with the high bran product and the level of calcium carbonate in the low fiber product is far less. The problems of handling the calcium carbonate are solved by altering the composition of the "inactive" flour components, to use cracked wheat and/or rice flour in place of all or part of the wheat flour in the original formulation. At this point, the low fiber product does not contain added iron. The low fiber product and the high fiber product are available in unflavored form, flavored with barbeque flavorant and flavored with beef-and-onion flavorant. The compositions were:

TABLE VII

| Ingredients | High Fiber Product (with bran) % | Amount per 100 gm package | Low Fiber Product (non-bran) % | Amount per 50 gm package |
|---|---|---|---|---|
| Bran (Wheat) | 50 | 50 gms | 0 | 0 |
| Riboflavin | 0.02 | 20 mg | 0.04 | 20 mg |
| Calcium Carbonate | 1.25 | 1.25 gm | 0.50 | 250 mg |
| (40% calcium content) | (0.5) | (500 mg) | (0.20) | (100 mg) |
| Reduced Iron | 0.01 | 10 mg | 0 | 0 |
| Cracked Wheat or Rice Flour | about 42 | about 42 gm | about 88 | about 44 gm |
| Coconut oil | 3 | 3 gm | 6 | 3 gm |
| Seasoning or Flavorant (where applicable) | 3 | 3 gm | 6 | 3 gm |

It is decided that it is better to use a combination of rice flour and whole wheat flour (Graham flour), so the following compositions are prepared:

TABLE VIII

| Ingredients | High Fiber Composition, Percent (Approx.) | Low Fiber Composition, Percent (Approx.) |
|---|---|---|
| Graham Flour | 40.0 | 80.0 |
| Rice Flour | 10.0 | 20.0 |
| Bran | 50.0 | 0 |
| Calcium Carbonate | 1.25 | 0.5 |
| Reduced Iron | 0.013 | 0 |
| Riboflavin | 0.02 | 0.04 |

To provide a better control as the long term investigation progressed, i.e., after about one year, it is decided to also fortify the control with an equivalent daily intake amount of reduced iron. So the following compositions are prepared for further use in the long term investigation:

TABLE IX

| Ingredients | High Fiber Product (with bran) % | Amount per 100 gm package | Low Fiber Product (non-bran) % | Amount per 50 gm package |
|---|---|---|---|---|
| Bran (Wheat) | 50 | 50 gms | 0 | 0 |
| Riboflavin | 0.02 | 20 mg | 0.04 | 20 mg |
| Calcium Carbonate | 1.25 | 1.25 gm | 0.50 | 250 mg |
| (40% calcium content) | (0.5) | (500 mg) | (0.20) | (100 mg) |
| Reduced Iron | 0.01 | 10 mg | 0.02 | 10 mg |
| Cracked Wheat or Rice Flour | about 42 | about 42 gm | about 88 | about 44 |

TABLE IX-continued

| Ingredients | High Fiber Product (with bran) % | Amount per 100 gm package | Low Fiber Product (non-bran) % | Amount per 50 gm package |
|---|---|---|---|---|
| Coconut oil | 3 | 3 gm | 6 | 3 gm |
| Seasoning or Flavorant (where applicable) | 3 | 3 gm | 6 | 3 gm |

Both of the compositions were prepared without any flavorant, with beef-and-onion flavorant and with barbeque flavorant.

The following is the latest extruded portion of the formulations used in the long term investigation:

TABLE X

| Ingredients | Low Fiber Composition | High Fiber Composition |
|---|---|---|
| Wheat Bran | 0 | 200 lbs. |
| Graham Flour | 400 lbs. | 160 lbs. |
| Rice Flour | 100 lbs. | 40 lbs. |
| Calcium Carbonate | 2 lbs. | 5 lbs. |
| Reduced Iron | 50 gm | 25 gm |
| Riboflavin | 90 gm | 36 gm |

Both compositions are extruded using a twin-screw speed of 150 rpm and are baked in an oven at 700° C. at 15 rpm. The high fiber composition has a standard plate count of 200 and an aerobic plate count/gram of 10; and the low fiber composition has a standard plate count of 50 and an aerobic plate count/gram of 30.

Both compositions are extruded in a cooker extruder having a rectangular shaped die opening to provide direct expanded products. As each of the compositions exits from the die, it curls and expands in all directions and is immediately cut into short pieces. Both extruded compositions are more puffed (i.e., more expanded) than are the earlier compositions. A conventional enrober is used to apply the oil to heated extrudate pieces and then the flavorant powder was applied.

The long term test is progressing using the latest snack formulations. The test is based on the point that, in the case of colorectal cancer, colorectal polyps can serve as a suitable precursor for the malignant disease. Briefly, the malignant potential on the adenoma is well recognized, and while that of the adenomatous and tubulovillous type is still debated, these three histologic types have each been observed with a cytologic atypia associated with malignancy. Further, while polyps can progress to malignancy, remain benign, or regress, patients with polyps are at an increased risk of additional polyps and of colorectal cancer, and the risk increased with the size and number of polyps.

Figure 2:
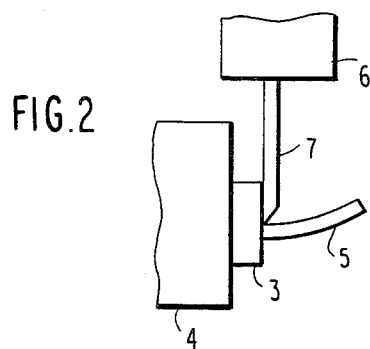
FIG. 2 is a side schematic view of the extrudate of the invention as it leaves the extruder fie and
FIG. 3 is a side view of the extruded food composition of the invention.
Figure 3:

In FIG. 1, numeral 1 represents a die (for a cooker extruder) having rectangular opening 2. In FIG. 2, the snack exits die 2 in end 3 of extruder barrel 4 as continuous material 5. Note the upwards curling of continuous material 5. Reciprocating blade 7 of cutter 6 is used to cut continuous material 5 into individual pieces 8 (see FIG. 3).

What is claimed is:
1. Food composition in the form of extrusion-cooked extrudate pieces, comprised of:
  (a) about 40 to about 70 weight percent of bran flour;
  (b) about 20 to about 50 weight percent of whole wheat flour;
  (c) about 5 to about 15 weight percent of rice flour;
  (d) about 0.5 to about 3 weight percent of calcium carbonate;
  (e) about 0.03 to about 0.005 weight percent of reduced iron; and
  (f) about 0.1 to about 0.005 weight percent of riboflavin,
the weight percents of ingredients (a) to (f) being based on the total dry weight of said food composition.

2. The food composition as claimed in claim 1 wherein the bran flour is whole wheat bran or corn bran.

3. The food composition as claimed in claim 1 wherein about 50 weight percent of bran flour is present.

4. The food composition as claimed in claim 1 wherein about 40 weight percent of whole wheat flour is present.

5. The food composition as claimed in claim 1 wherein about 10 weight percent of rice flour is present.

6. The food composition as claimed in claim 1 wherein about 1.25 weight percent of calcium carbonate is present.

7. The food composition as claimed in claim 1 wherein about 0.013 weight percent of reduced iron is present.

8. The food composition as claimed in claim 1 wherein about 0.02 weight percent of riboflavin is present.

9. Food composition comprised of:
(A) extrusion-cooked extrudate pieces, comprised of:
  (a) about 40 to about 70 weight percent of bran flour;
  (b) about 20 to about 50 weight percent of whole wheat flour;
  (c) about 5 to about 15 weight percent of rice flour;
  (d) about 0.5 to about 3 weight percent of calcium carbonate;
  (e) about 0.03 to about 0.005 weight percent of reduced iron; and
  (f) about 0.1 to about 0.005 weight percent of riboflavin,
the weight percents of ingredients (a) to (f) being based on the total dry weight of said food composition;
(B) a layer of about 1 to about 10 weight percent of an edible organic oil on each of the extrudate pieces, the weight percent of said organic oil being based on the total dry weight of said food composition; and
(C) about 1 to about 10 weight percent of particulate flavorant on the outer surface of said extrudate pieces, said particulate flavorant being adhered to said extrudate pieces by said organic oil, the weight percent of said particulate flavorant being based on the total dry weight of said food composition.

10. The food composition as claimed in claim 9 wherein the organic oil is coconut oil.

11. The food composition as claimed in claim 9 wherein about 3 weight percent of the organic oil is present.

12. The food composition as claimed in claim 9 wherein the particulate flavorant is in powder form.

13. The food composition as claimed in claim 9 wherein about 3 weight percent of the particulate flavorant is present.

14. The food composition as claimed in claim 9 wherein the bran flour is whole wheat bran or corn bran.

15. The food composition as claimed in claim 9 wherein about 50 weight percent of bran flour is present.

16. The food composition as claimed in claim 9 wherein about 40 weight percent of whole wheat flour is present.

17. The food composition as claimed in claim 9 wherein about 10 weight percent of rice flour is present.

18. The food composition as claimed in claim 9 wherein about 1.25 weight percent of calcium carbonate is present.

19. The food composition as claimed in claim 9 wherein about 0.013 weight percent of reduced iron is present.

20. The food composition as claimed in claim 9 wherein about 0.02 weight percent of riboflavin is present.

21. Process of preventing the occurrence of colorectal polyps in a human, except for one who is genetically incapable of developing colorectal polyps, comprised of consuming the food composition of claim 1 by said human on a daily basis over an extended period of time, the amount of said food composition consumed by said human being an amount effective to prevent the occurrence of colorectal polyps in said human.

22. Process as claimed in claim 21 wherein the occurrence colon polyps is prevented.

23. Process as claimed in claim 21 wherein the occurrence of rectal polyps is prevented.

24. Process of preventing the occurrence of colorectal polyps in a human, except for one who is genetically incapable of developing colorectal polyps, comprised of consuming the food composition of claim 9 by said human on a daily basis over an extended period of time, the amount of said food composition consumed by said human being an amount effective to prevent the occurrence of colorectal polyps in said human.

25. Process as claimed in claim 24 wherein the occurrence colon polyps is prevented.

26. Process as claimed in claim 24 wherein the occurrence of rectal polyps is prevented.

27. Process of preventing the recurrence of colorectal polyps in a human, except one who is genetically incapable of developing colorectal polyps, comprised of consuming the food composition of claim 1 by said human on a daily basis over an extended period of time, the amount of said food composition consumed by said human being an amount effective to prevent the recurrence of colorectal polyps in said human.

28. Process as claimed in claim 27 wherein the recurrence of colon polyps is prevented.

29. Process as claimed in claim 27 wherein the recurrence of rectal polyps is prevented.

30. Process of preventing the recurrence of colorectal polyps in a human, except one who is genetically incapable of developing colorectal polyps, comprised of consuming the food composition of claim 9 by said human on a daily basis over an extended period of time, the amount of said food composition consumed by said human being an amount effective to prevent the recurrence of colorectal polyps in said human.

31. Process as claimed in claim 30 wherein the recurrence of colon polyps is prevented.

32. Process as claimed in claim 30 wherein the recurrence of rectal polyps is prevented.

33. Process of preventing colorectal cancer in a human, except one who is genetically incapable of developing colorectal cancer, comprised of consuming the food composition of claim 1 by said human on a daily basis over an extended period of time, the amount of said food composition consumed by said human being an amount effective to prevent colorectal cancer in said human.

34. Process as claimed in claim 33 wherein colon cancer is prevented.

35. Process as claimed in claim 33 wherein rectal cancer is prevented.

36. Process of preventing colorectal cancer in a human, except one who is genetically incapable of developing colorectal cancer, comprised of consuming the food composition of claim 9 by said human on a daily basis over an extended period of time, the amount of said food composition consumed by said human being an amount effective to prevent colorectal cancer in said human.

37. Process as claimed in claim 36 wherein colon cancer is prevented.

38. Process as claimed in claim 36 wherein rectal cancer is prevented.

39. Process for preparing a food composition in the form of extrusion-cooked extrudate pieces, comprised of:
   (a) admixing:
      (i) about 40 to about 70 weight percent of bran flour;
      (ii) about 20 to about 50 weight percent of whole wheat flour;
      (iii) about 5 to about 15 weight percent of rice flour;
      (iv) about 0.5 to about 3 weight percent of calcium carbonate;
      (v) about 0.03 to about 0.005 weight percent of reduced iron;
      (vi) about 0.1 to about 0.005 weight percent of riboflavin; and
      (vii) about 1 to about 10 weight percent of water, the weight percents of ingredients (i) to (ii) being based on the total dry weight of said food composition; and
   (b) extruding said wetted admixture in said cooker extruder to form said extrusion-cooked extrudate pieces.

40. The process as claimed in claim 39 wherein said admixing is done in a ribbon blender.

41. The process as claimed in claim 39 wherein ingredients (i) to (vi) are first admixed and feed to said cooker extruder, and then water (vii) is admixed with the mixture of ingredients (i) to (vi) in said cooler extruder.

42. Process for preparing a food composition in the form of coated, extrusion-cooked extrudate pieces, comprised of:
   (a) admixing:
      (i) about 40 to about 70 weight percent of bran flour;
      (ii) about 20 to about 50 weight percent of whole wheat flour;
      (iii) about 5 to about 15 weight percent of rice flour;
      (iv) about 0.5 to about 3 weight percent of calcium carbonate;
      (v) about 0.03 to about 0.005 weight percent of reduced iron;
      (vi) about 0.1 to about 0.005 weight percent of riboflavin; and
      (vii) about 1 to about 10 weight percent of water, the weight percents of ingredients (i) to (ii) being based on the total dry weight of said food composition;

(b) extruding said wetted admixture in said cooker extruder to form said extrusion-cooked extrudate pieces;

(c) placing a layer of about 1 to about 10 weight percent of an edible oil on each of the extrudate pieces, the weight percent of said organic oil being based on the total dry weight of said food composition; and (d) placing about 1 to about 10 weight percent of particulate flavorant on the extrudate pieces, said particulate flavorant being adhered to the extrudate pieces by the organic oil, the weight percent of the particulate flavorant being based on the total dry weight of said food composition.

43. The process as claimed in claim 42 wherein said admixing is done in a ribbon blender.

44. The process as claimed in claim 43 wherein ingredients (i) to (vi) are first admixed and feed to said cooker extruder, and then water (vii) is admixed with the mixture of ingredients (i) to (vi) in said cooker extruder.

45. The process as claimed in claim 42 wherein the oil layer is sprayed on the extrudate pieces.

46. The process as claimed in claim 45 wherein the particulate flavorant is placed on the oil coated extrudate pieces.

* * * * *